US005530162A

United States Patent [19]
Rothwell et al.

[11] Patent Number: 5,530,162
[45] Date of Patent: Jun. 25, 1996

[54] PROCESS FOR THE HYDROGENATION OF ARYL PHOSPHINES AND PRODUCTS OBTAINED THEREFROM

[75] Inventors: Ian P. Rothwell, West Lafayette, Ind.; S. Joyce Yu, Taipei, Taiwan

[73] Assignee: Research Corporation Technologies, Inc., Tucson, Ariz.

[21] Appl. No.: 90,085

[22] PCT Filed: Apr. 13, 1993

[86] PCT No.: PCT/US93/03453

§ 371 Date: Jul. 21, 1993

§ 102(e) Date: Jul. 21, 1993

[87] PCT Pub. No.: WO93/21192

PCT Pub. Date: Oct. 28, 1993

Related U.S. Application Data

[63] Continuation-in-part of Ser. No. 867,948, Apr. 13, 1992, abandoned.

[51] Int. Cl.$^6$ .................................. C07F 9/50; C08F 8/04
[52] U.S. Cl. ............................................................ 568/8
[58] Field of Search ...................................... 568/8

[56] References Cited

U.S. PATENT DOCUMENTS

| | | | |
|---|---|---|---|
| 4,010,181 | 3/1977 | Aviron-Violet | 260/326 |
| 4,216,331 | 8/1980 | Henderson, Jr. | 548/320 |
| 4,440,936 | 4/1984 | Riley | 548/498 |
| 4,654,176 | 3/1987 | Dang et al. | 260/505 |
| 4,845,306 | 7/1989 | Puckette | 568/454 |
| 5,021,593 | 6/1991 | Nohira et al. | 556/20 |

OTHER PUBLICATIONS

Chesnut et al., "Mechanistic Study of the Cyclometalation of o–Arylphenoxide ligands at Group 5 metal Centers," *Organometallics*, 10: 321–328 (1991).

Yamamoto et al., "New Entry to the Preparation of Chiral Bis(Dicyclohexylphosphino) Alkane Derivatives. Use for Rhodium–Catalyzed Hydrogenation of Carbonyl Compounds," *Chem. Let.*, 9: 1603–1606 (1984).

Yu et al., "All–Cis Catalytic Hydrogenation of Polynuclear Aromatic Hydrocarbons by Group 5 Metal Aryloxide Compounds," *J. Am. Chem. Soc.*, 114: 1927–1929 (1992).

Ankianiec et al., "Isolation of a New Series of Seven–Coordinate Hydride Compounds of Tantalum(V) and Their Involvement in the Catalytic Hydrogenation of Arene Rings," *J. Am. Chem. Soc.*, 113: 4710–4712 (1991).

*Chem. Abstracts*, 94, No. 8, Abstract No. 55044 (Feb. 23, 1981).

Gordon et al., "Phosphorus–31 Nuclear Magnetic Resonance Spectroscopy in the Determination of Conformational Free Energies of Phosphorus Groups on the Cyclohexane Ring," *J. Am. Chem. Soc.*, 98: 15–23 (1976).

Yu et al., "Catalytic Hydrogenation of Aryl Phosphines by Niobium Aryloxide Compounds: High Yield and Efficient Synthesis of Cyclohexyl Phosphine Ligands," *J. Chem. Soc., Chem. Commun.*, 8: 632–633 (1992).

*Primary Examiner*—James H. Reamer
*Attorney, Agent, or Firm*—Scully, Scott, Murphy & Presser

[57] ABSTRACT

A process for making a cycloalkyl phosphine comprising hydrogenating an aryl phosphine in the presence of an effective amount of an aryloxide of a metal selected from the group consisting of niobium and tantalum is disclosed. Cycloalkyl phosphine products of this process, useful as ligands in a complex of a transition metal which acts as a catalyst in the formation of stereoisomers, are also set forth. Furthermore, niobium or tantalum organometallic compounds, generated in this process, useful in the catalytic hydrogenation of aryl phosphines and arene-containing polymers, is also described.

38 Claims, No Drawings

PROCESS FOR THE HYDROGENATION OF ARYL PHOSPHINES AND PRODUCTS OBTAINED THEREFROM

STATEMENT AS TO RIGHTS TO INVENTION MADE UNDER FEDERALLY-SPONSORED RESEARCH AND DEVELOPMENT

This invention was made with the support of the U.S. Government under Grant No. CHE-8915573 awarded by the National Science Foundation. The U.S. Government has certain rights in this invention.

CROSS-REFERENCE TO RELATED APPLICATION

This is a continuation-in-part of U.S. patent application Ser. No. 867,948 filed Apr. 13, 1992, now abandoned.

BACKGROUND OF THE DISCLOSURE

1. Field of the Invention

Phosphine ligands play a critical role in organic and organometallic chemistry and find important application as ancillary phosphine ligands attached to transition metals. Important chemical processes rely on chiral phosphine ligands to carry out asymmetric hydrogenation, isomerization and related reactions. These reactions lead to new products, some of which are chiral and represent new and exciting medicines and drugs useful in the pharmaceutical industry.

Until now, the vast majority of available phosphine ligands useful in these catalytic processes were aryl phosphines. The reason for the use of aryl substituents in the prior art was, in addition to their reasonable effectiveness, their availability. On the other hand, the prior art methods of synthesizing phosphine ligands containing alkyl substituents is very difficult and inefficient. However, the last few years have evidenced a growing interest in phosphine ligands containing alkyl substituents. This interest has been spurred by the growing belief that the use of alkyl substituents, of which cyclohexyl is a prime example, provide an environment wherein catalytic processes for obtaining chiral type products is enhanced.

As stated above, there are processes to produce cycloalkyl phosphines. However, these processes are complex and thus produce cycloalkyl phosphines in low yield and low purity. Thus, a process for the production of cycloalkyl phosphines, particularly cyclohexyl phosphines, in high yield and high purity, is a need well recognized in the art.

2. Background of the Prior Art

Processes to make asymmetrical phosphines and diphosphines which are useful in forming complexes with transition metals having optically active coordinating groups are known in the art. U.S. Pat. No. 4,010,181 to Aviron-Violet provides a process for making diphosphines, in which the phosphorus atoms are linked to a cycloalkyl group, by contacting a sulfonic acid ester of a stereoisomer of trans-bis-(1,2-hydroxymethyl)-cyclobutene with an alkali metal phosphide. The synthesis of these reactant involve difficult preparation schemes. The product of this process is recited to be useful as a ligand in the formation of rhodium complexes which act as catalysts in the hydrogenation of substituted acrylic acids and acid esters to produce optically active propionic acid derivatives.

U.S. Pat. No. 4,216,331 to Henderson, Jr. describes a chiral bisphosphine-rhodium complex which complex acts as a catalyst for the asymmetrical reduction of a tetramisole precursor leading to the synthesis of levamisole in high optical yield. The chiral bisphosphine is obtained by reacting a chiral enantiomer of trans-2,3-bis(diphenylphosphinomethyl)bicyclo[2.2.1]heptane with a rhodium complex.

U.S. Pat. No. 4,440,936 to Riley describes a chiral phosphine ligand which when complexed with rhodium functions as a superior chiral hydrogenation catalyst. The chiral phosphine ligand component of the catalyst is formed in a four-step process that finally results in the formation of a cyclohexyl-containing phosphine which provides a yield of about 30%.

U.S. Pat. No. 4,654,176 to Dang et al. discloses novel sulfonated chiral phosphines which in many embodiments includes a cycloalkyl constituent. These phosphines are obtained by the sulfonation of a phosphine substituted with an aryl group and two straight, branched or cyclic alkyls, one of which is chiral.

U.S. Pat. No. 5,021,593 to Nohira et al. sets forth a ruthenium-containing optically active phosphine complex which includes the ligand 2,2'-bis(dicyclohexylphosphino)-6,6'-dimethyl-1,1'-biphenyl (BICHEP). The BICHEP ligand is prepared in a complex process involving 13 steps.

Of interest in the process of this invention is the paper, Chesnut et al., *Organometallics*, 10, 321–328 (October, 1991). This paper sets forth a method for making a class of niobium and tantalum aryloxides. The metal aryloxides are characterized by NMR spectropscopy.

There are additional processes known in the art for making cycloalkyl substituted phosphines. However, the last mentioned Nohiro et al. patent illustrates the complexity of these processes and the strong need in the art for simpler and effective methods of forming cycloalkyl-substituted phosphine ligands useful in the formation of transition metal-containing optically active complexes useful in the catalytic formation of important chiral compounds.

BRIEF SUMMARY OF THE INVENTION

A new process has now been discovered which produces cycloalkyl phosphines in high yield and high purity occasioned by the absence of a plurality of reaction steps and purification operations. This new process employs readily available aryl phosphines as starting reactants rather than complex, non-commercially available compounds obtained only by difficult synthesis.

In accordance with the present invention a process for making a cycloalkyl phosphine is provided. In this process an aryl phosphine is hydrogenated in the presence of an effective amount of an aryloxide of a metal selected from the group consisting of niobium and tantalum.

In further accordance with the present invention a class of organometallic compounds, useful in the process of this invention, is provided. These compounds have the structural formula $M(H)_y(ORT^7)_{5-y}(L)_z$, where M is niobium or tantalum; $R^7$ is hydrocarbyl; L is $PR^8R^9R^{10}$; y is 1, 2 or 3; z is 0, 1 or 2; and $R^8$, $R^9$ and $R^{10}$ are the same or different and are hydrocarbyl.

In still further accordance with the instant invention cycloalkyl phosphine compounds, products made in accordance with the process of the present invention, are disclosed. These compounds are selected from the group consisting of a compound having the structural formula $P(R^{11})_{3-w}(cy)_w$, where $R^{11}$ is hydrocarbyl having chiral properties; cy is cyclohexyl; and w is 1 or 2; $R^{12}P(Ph)(cy)$ where $R^{12}$ is hydrocarbyl; Ph is phenyl; and cy is cyclohexyl; and $R^{13}R^{14}$, where $R^{13}$ is hydrocarbyl; and $R^{14}$ is cyclohexyl or tetrahydronaphthyl substituted at the α or β position.

DETAILED DESCRIPTION

The novel process of the present invention employs aryl phosphines as reactants which are hydrogenated to produce cycloalkyl phosphines, particularly cyclohexyl phosphines. As discussed in the Background of the Disclosure such aryl phosphines have been, in the past, employed as ligands in transition metal complexes, which complexes act as optically active catalysts and the like.

Among the aryl phosphines within the contemplation of this invention are trihydrocarbyl phosphines wherein at least one of the three hydrocarbyl groups is aryl. Preferably, the aryl hydrocarbyl group is phenyl.

In a preferred embodiment wherein a trihydrocarbyl phosphine, of which one of the three hydrocarbyl groups is phenyl, is employed, the phosphine compound has the structural formula

$$P(R^2)_x(R^3)_{3-x} \qquad (I)$$

where $R^2$ is phenyl; $R^3$ is alkyl, aralkyl or alkenyl; and x is an integer of 1 to 3.

More preferably, the compound having the structural formula I is characterized by $R^3$ being methyl, ethyl, ethenyl or benzyl.

A second class of aryl phosphines useful in the process of the present application of manufacturing cycloalkyl phosphines is characterized by the structural formula:

$$(R^4)_2P(R^5)_sP(R^4)_2 \qquad (II)$$

where $R^4$ is aryl; $R^5$ is alkylene or substituted alkylene; and s is an integer of 1 to 6.

Preferably, the compound having the structural formula II is characterized by $R^4$ being phenyl; and $R^5$ being methylene. In another preferred embodiment of the compound having the structural formula II, $R^5$ is methylene including at least one substituted methyl group. In a particularly preferred embodiment of the process of the present invention wherein an aryl phosphine having the structural formula II is employed, $R^4$ is phenyl; $R^5$ is $-CH(CH_3)CH_2CH(CH_3)$; and s is 1.

Yet another preferred class of aryl phosphines is the class of 1,1,1-tris(dephenylphosphino)alkanes. Preferably, this class encompass 1,1,1-tris(diphenyl-phosphino)$C_1$–$C_3$ alkanes. More preferably, this class of compounds includes 1,1,1-tris(diphenylphosphino)methane and 1,1,1-tris(diphenylphosphino)ethane.

Independent of the choice of aryl phosphine utilized in the process of the present invention, it is contacted with hydrogen gas in a hydrogenation reaction. The hydrogen gas which contacts the phosphine is preferably at a pressure above at least about 100 psi and at a temperature above at least about 50° C. More preferably, the thermodynamic conditions under which the aryl phosphine and hydrogen gas react is at a pressure in the range of between about 500 psi and about 1500 psi and at a temperature in the range of between about 80° C. and about 100° C. Still more preferably, the thermodynamic conditions under which the hydrogenation reaction occurs is a pressure in the range of between about 1000 psi and about 1400 psi and a temperature in the range of between about 80° C. and about 100° C. Even still more preferably, the pressure of the hydrogenation reaction is between about 1100 psi and about 1300 psi.

It is desirable to conduct the contact between the aryl phosphine and the hydrogen gas in solution. That is, the aryl phosphine contacts the hydrogen gas, in a preferred embodiment, dissolved in an organic solvent. Preferably, the organic solvent is a liquid hydrocarbon. More preferably, the liquid hydrocarbon is a $C_5$ to $C_8$ alkane. A particularly preferred alkane within the contemplation of this invention is cyclohexane.

A critical aspect of the process of the present invention is the employment of an agent to facilitate the hydrogenation reaction of the aryl phosphine. In the process of the present invention this agent is an aryloxide of a metal selected from the group consisting of niobium and tantalum. Preferably, the agent employed in the process of the present invention is a compound having the structural formula

$$M(OR)_n(R^1)_{5-n} \qquad (III)$$

where M is niobium or tantalum; R is aryl or alkaryl; $R^1$ is alkyl, aralkyl, alkarylalkyl, silylalkyl, hydrogen or halogen; and n is 2 or 3, with the proviso that if $R^1$ is halogen, a cocatalyst selected from the group consisting of an alkali metal hydrocarbyl, an alkaline earth metal hydrocarbyl, a zinc hydrocarbyl, an aluminum hydrocarbyl, a hydrocarbylsilane, an alkali metal boron hydride, an alkali metal aluminum hydride and an aluminum hydrocarbyl hydride is included with the first catalyst, the compound having the structural formula III.

In a preferred embodiment, the compound having the structural formula III is characterized by R having the meanings di-$C_1$–$C_4$ alkylphenyl, di-$C_3$–$C_8$ cycloalkylphenyl or diphenylphenyl.

Yet more preferably, R is 2,6-di-$C_1$–$C_3$ alkylphenyl, 2,6-di-$C_3$–$C_6$ cycloalkylphenyl or 2,6-diphenylphenyl in the compound having the structural formula III.

Even more preferably, R in structural formula III has the meanings 2,6-diisopropylphenyl, 2,6-dicyclohexylphenyl, 2,6-dimethylphenyl or 2,6-diphenylphenyl.

Preferred substituents having the meaning $R^1$ include $C_1$ to $C_4$ alkyl, benzyl, phenylbenzyl, $C_1$ to $C_2$ alkylbenzyl, tri-$C_1$ to $C_2$ alkylsilylmethyl, hydrogen, or chlorine.

Although the use of a compound in which the metal M in structural formula III is niobium or tantalum is equally effective, niobium is more preferred. Analogously, although the use of a compound having the structural formula III where n is 2 or 3 is equally effective, the employment of a compound having the structural formula III where n is 2 is more preferred.

As stated above in the preferred embodiment of the compound having the structural formula III wherein $R^1$ is halogen or, more preferably, chlorine, a cocatalyst is employed. Of the cocatalysts within the contemplation of the present invention, it is preferred that this compound be selected from the group consisting of $LiR^6$, $MgR^6$, $MgClR^6$, $ZnR^6_2$, $AlR^6_3$, sodium boron hydride, lithium boron hydride, lithium aluminum hydride, lithium triethyl hydride and diisobutyl aluminum hydride.

Another aspect of the present invention is the formation of a new class of organometallic compounds having the structural formula

$$M(H)_y(OR^7)_{5-y}(L)_z \qquad (IV)$$

where M is niobium or tantalum; $R^7$ is hydrocarbyl; L is $PR^8R^9R^{10}$; y is an integer of 1 to 3; z is 0 or an integer of 1 or 2; and $R^8$, $R^9$ and $R^{10}$ are the same or different and are hydrocarbyl. Obviously, the identity of this compound is a function of the compound III from which this compound is derived.

Preferably the organometallic compound of the present invention has the structural formula IV where $R^7$ is alkyl, aryl or alkaryl; and $R^8$, $R^9$ and $R^{10}$ are the same or different and are alkyl, aryl or alkaryl.

More preferably, at least one of $R^7$, $R^8$, $R^9$ and $R^{10}$ is chiral alkyl, chiral aryl or chiral alkaryl.

The organometallic compound having the structural formula IV is recovered in the process of the present invention. This compound is useful as a catalytic agent in the hydrogenation of aryl phosphines to produce cyclohexyl phosphines. Although the inventors emphasize that the theory under which the process proceeds is not part of the invention it is theorized that the compound having the structural formula III is converted during the reaction to the organometallic compound having the structural formula IV.

Still another aspect of the present invention is a class of cyclohexyl phosphines having the structural formula

$$P(R^{11})_{3-w}(cy)_w \qquad (v)$$

wherein $R^{11}$ is chiral hydrocarbyl; cy is cyclohexyl; and w is an integer of 1 or 2.

These compounds, having the structural formula V, synthesized in accordance with the present invention, are preferably limited by the requirement that $R^{11}$ is chiral aryl, chiral alkyl, chiral alkaryl or chiral aralkyl.

A further aspect of this invention is a further class of compounds made in accordance with the process of the present application. These compounds have the structural formula

$$R^{12}P(Ph)(cy) \qquad (VI)$$

where $R^{12}$ is hydrocarbyl; Ph is phenyl; and cy is cyclohexyl. Preferably, $R^{12}$ is aryl, alkyl, alkaryl or aralkyl. More preferably, $R^{12}$ is chiral alkyl, chiral aryl, chiral alkaryl or chiral aralkyl.

In yet still another aspect of the present invention a further class of compounds is provided. This class of compounds, made in accordance with the process of the present invention, has the structural formula

$$R^{13}{}_2PR^{14} \qquad (VII)$$

where $R^{13}$ is hydrocarbyl; and $R^{14}$ is cyclohexyl or tetrahydronaphthyl substituted at the α or β position.

Preferably, the compound having the structural formula VII is characterized by $R^{13}$ being alkyl, aryl, alkaryl or aralkyl; and $R^{14}$ being cyclohexyl substituted at the 2 or 3 position.

Still more preferably, the meaning of $R^{13}$ in structural formula VII is chiral alkyl, chiral aryl, chiral alkaryl or chiral aralkyl.

It is emphasized that compounds V, VI and VII are products of the process of this invention. Obviously, the production of compounds having the structural formulae V, VI and VII are obtained as a function of the aryl phosphine reactant employed in the process of this invention.

The class of organometallic compounds of the present invention having structural formula IV finds significant utility in catalyzing the hydrogenation of arene-containing polymers to produce cycloaliphatic-containing polymers. Those skilled in the art are aware of the clear line of distinction between a polymer that includes arene groups compared to an otherwise identical polymer but for the replacement of arene groups with cycloaliphatic groups.

A particularly commercially important class of polymers which include arene groups are styrene polymers. Specifically, styrene homopolymers, i.e. polystyrene and styrene derivative homopolymers, such as alkyl-substituted styrene homopolymers and styrene copolymers, i.e. styrene-butadiene copolymers and acrylonitrile-butadiene styrene copolymers (ABS) and the like, are commercially important polymers whose properties can be altered to produce polymers having desirable properties not provided by the phenyl group-containing styrene polymers.

Of the styrene polymers probably the most important from the point of view of hydrogenation, are the elastomeric type styrene-butadiene copolymers. These polymers are not only provided with important new characteristics by the exhaustive hydrogenation of its phenyl groups but, in addition, those skilled in the art are aware of the incomplete saturation of the aliphatic backbone of this polymer. The catalytic use of the organometallic compounds of the present invention selectively saturates this backbone which overcomes a major detrimental property of these elastomers, their oxidative instability.

The organometallic compounds of the present invention represent an advance in the art over the presently employed catalysts for the hydrogenation of arene-containing polymers particularly the styrene polymers and more particularly styrene-butadiene copolymers. This is so in that the organometallic compounds of the present invention are at least as effective as the presently employed catalyst used in this process. At present two types of metal catalysts are employed in this application. Both classes of metals used in these catalysts are Group VIII metals. It is emphasized that the organometallic compound of the present invention includes niobium or tantalum as the metal. Niobium and tantalum are Group V metals and are thus clearly distinguished from the Group VIII metals of the prior art.

It is furthermore emphasized that the environmental dangers posed by one of the two classes of prior art Group VIII metal hydrogenation catalysts, the nickel-containing catalyst systems and the exceedingly high cost processing involved in the use of the second class of Group VIII metals, the platinum group metal-containing catalyst systems, is overcome by the use of the organometallic compounds of the present invention. Specifically, the organometallic compounds having the structural formula IV provide a relatively low cost, environmentally safe hydrogenation catalyst.

The following examples are given to illustrate the scope of the present invention. Because these examples are given for illustrative purposes, the invention should not be deemed limited thereto.

EXAMPLE 1

Synthesis of Bis(di-cyclohexylphosphino)methane

A 300 ml. stainless steel high pressure reactor was charged, under a nitrogen atmosphere at atmospheric temperature, with a solution of

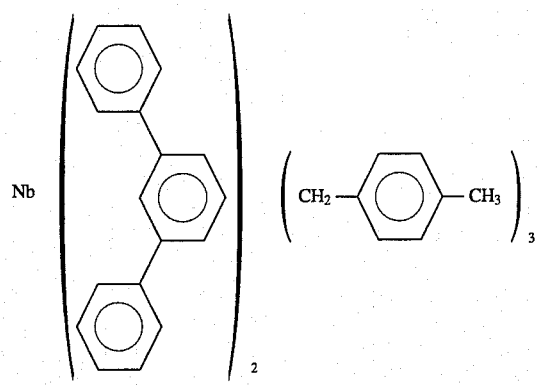

hereinafter referred to as Nb(OC$_6$H$_3$Ph$_2$—2, 6)$_2$(CH$_2$C$_6$H$_4$—4Me)$_3$ (2.2 g., 2.5 mmol.) and bis(di-phenylphosphino)methane (25.0 g., 65.1 mmol.) in cyclohexane (55 ml.). The reactor was pressurized with hydrogen (1,200 psi) and heated at 100° C. for four days. During the course of the reaction the pressure dropped requiring the repressurization of the reactor four times. Thereupon, the reactor was cooled and the hydrogen gas vented. The cyclohexane was removed in vacuo and water (30 ml.) was added to the mixture. The mixture was extracted with diethyl ether (200 ml.) which extraction was repeated four times to yield a clear colorless solution. The ether was removed and the resultant solution was recrystallized from hot ethanol (120 ml.).

The product, bis(di-dicyclohexylphosphino)methane, was obtained as white crystals (25.5 g., 62.4 mmol.). This represented a yield of 96% of theoretical.

EXAMPLE 2

Synthesis of Bis(di-cyclohexylphosphino)butane

Example 1 was reproduced with the substitution of bis(diphenylphosphino)butane (10 g., 23 mmol.) for the bis(diphenylphosphino)butane of Example 1. The process employed was identical with Example 1 but for the reduction in the period of hydrogenation from 4 days in Example 1 to 2 days in this example. In addition, the temperature of the hydrogenation reaction was reduced from 100° C. to 80° C. Other distinctions involved a reduction in the amount of Nb(OC$_6$H$_3$Ph$_2$—2,6)$_2$(CH$_2$C$_6$H$_4$—4Me)$_3$ (1.0 g, 1.1 mmol.) and cyclohexane solvent (15 ml.).

The product bis(di-cyclohexylphosphino)butane, was obtained in an amount of 8.9 g. (19.3 mmol.), representative of a yield of 85%.

EXAMPLE 3

Synthesis of Tris (di-cyclohexylphosphinomethyl) ethane

Example 1 was repeated except that the niobium compound, Nb(OC$_6$H$_3$Ph$_2$—2,6)$_2$(CH$_2$H$_6$H$_4$—4Me)$_3$ (1.5 g., 1.6 mmol) was dissolved with this (diphenylphosphinomethyl)ethane (4.6 g., 7.5 mmol.) in cyclohexane (15 ml.) and reacted for 2 days at 100° C.

The product of this hydrogenation reaction was tris(dicyclohexylphosphinomethyl)ethane (4.1 g., 6.4 mmol). This represented a yield of 85% of the theoretical.

EXAMPLE 4

Synthesis of Dimethylcyclohexyl Phosphine

The same reactor employed in Example 1 was charged with a solution of Nb(OC$_6$H$_3$Ph$_2$—2,6)$_2$(CH$_2$C$_6$H$_4$—4Me)$_3$(0.9 g, 0.1 mmol.) and dimethylphosphine phosphine (2 mmol.) in cyclohexane (3 ml.). The reactor was thereupon pressurized with hydrogen gas to a pressure of 1200 psi and maintained at this pressure and at a temperature of 80° C. for 24 hours.

The product of this reaction, obtained in accordance with the separation and purification steps described in Example 1, was dimethylcyclohexyl phosphine. This product was identified by $^{31}$P NMR in a yield of (2 mmol), 100% of the theoretical.

EXAMPLE 5

Synthesis of Dicyclohexylmethyl Phosphine

Example 4 was identically reproduced, including the same molar concentrations of all compounds utilized, with the exception that the dimethylphenyl phosphine of Example 4 was replaced with dephenylmethyl phosphine.

The product of this hydrogenation reaction was dicyclohexylmethyl phosphine obtained in a yield of 2 mmol., as determined by $^3$P NMR analysis, representative of a 100% yield.

EXAMPLE 6

Synthesis of Dicyclohexylcyclohexylmethyl Phosphine

Example 4 was identically reproduced but for the substitution of the diphenylbenzyl phosphine (0.3 mmol.) for the dimethylphenyl phosphine (2 mmol.) of Example 4.

The product of this reaction was dicyclohexylcyclohexylmethyl phosphine (0.3 mmol.) as determined by $^{31}$P NMR analysis. This represents a yield of 100% of that theoretically obtainable.

EXAMPLE 7

Synthesis of Tricyclohexyl Phosphine

Example 6 was identically reproduced in all respects but for the substitution of the aryl phosphine reactant. In the example the aryl phosphine was triphenyl phosphine (0.3 mmol.)

The product of this contact was tricyclohexylphosphine (0.3 mol.) as determined by $^{31}$P NMR spectroscopic analysis, representative of a yield of 100% of the theoretical.

EXAMPLE 8

Synthesis of Tri-4-methylcyclohexyl Phosphine

This example was conducted in accordance with Example 6 but for the identity of the aryl! phosphine as well as the reaction conditions. In this example the aryl phosphine utilized was tri-4-methylphenyl phosphine (0.3 mmol). In addition, the reaction, although still conducted a pressure of 1200 psi, was run at a higher temperature, 100° C. and conducted for 48 hours, rather than the 24 hours term of Example 6. Otherwise, the conditions that existed in Example 5 were identical.

The product of this reaction was tri-4-methycyclohexyl phosphine (0.3 mmol.). This determination was made by $^3$P NMR spectroscopic analysis. This analysis of further indicated the stereo chemistry of the resulting rings was as follows: 45%, (cis)$_3$; 38%, (cis)$_2$(trains); 14% (cis)(trans)$_2$; and 3%, (trans)$_3$.

EXAMPLE 9

Synthesis of Tri-2-methylcyclohexyl Phosphine

Example 8 was identically reproduced except that the aryl phosphine compound was tri-2-methylphenyl phosphine (0.3.)

The product of this reaction was again 100% pure tri-2-methylcyclohexyl phosphine, i.e. (0.3 mmol.), as determined by $^{31}$P NMR analysis. This analysis further indicated that the stereochemistry of the resulting rings was as follows: 57%, (cis)$_3$; 37%, (cis)$_2$(trans) and 6%, (cis)(trans)$_2$.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for making a cyclalkyl phosphine comprising hydrogenating an aryl phosphine in the presence of an effective amount of an aryloxide of a metal selected from the group consisting of niobium and tantalum.

2. A process in accordance with claim 1 wherein said cycloalkyl phosphine is a cyclohexyl phosphine.

3. A process in accordance with claim 1 wherein said metal aryloxide has the structural formula $M(OR)_n(R^1)_{5-n}$, where M is niobium or tantalum; R is aryl or alkaryl; $R^1$ is alkyl, cycloalkyl, aralkyl, alkarylalkyl, alkylsilylalkyl, hydrogen or halogen; n is 2 or 3, with the proviso that if $R^1$ is halogen, a cocatalyst selected from the group consisting of an alkali metal hydrocarbyl, an alkaline earth hydrocarbyl, a zinc hydrocarbyl, an aluminum hydrocarbyl, an alkali metal boron hydride, an aluminum hydride, an alkali metal aluminum trialkyl hydride and an alkyl aluminum hydride is present.

4. A process in accordance with claim 3 wherein R is di-$C_1$ to $C_4$ alkylphenyl, di-$C_3$ to $C_8$ cycloalkylphenyl or diphenylphenyl; and $R^1$ is $C_1$ to $C_4$ alkyl, benzyl, phenylbenzyl, $C_1$-$C_2$ alkylbenzyl, tri-$C_1$ to $C_2$ alkylsilylmethyl, hydrogen or chlorine.

5. A process in accordance with claim 4 wherein R is 2,6-di-$C_1$ to $C_3$ alkylphenyl, 2,6-di-$C_3$ to $C_6$ cycloalkylphenyl or 2,6-diphenylphenyl; and $R^1$ is methyl, ethyl, trimethylsilylmethyl, benzyl, 4-methylbenzyl, 4-ethylbenzyl, 4-phenylbenzyl, hydrogen or chlorine.

6. A process in accordance with claim 5 wherein R is 2,6-dimethylphenyl, 2,6-diisopropylphenyl, 2,6-dicyclohexylphenyl or 2,6-diphenylphenyl; and $R^1$ is methyl, trimethylsilylmethyl, benzyl, 4-methylbenzyl, 4-phenylbenzyl, hydrogen or chlorine.

7. A process in accordance with claim 6 where M is niobium.

8. A process in accordance with claim 7 wherein n is 2.

9. A process in accordance with claim 8 wherein R is 2,6-diphenylphenyl.

10. A process in accordance with claim 1 wherein said aryl phosphine is a trihydrocarbyl phosphine with the proviso that at least one of the hydrocarbyl groups is aryl or alkaryl.

11. A process in accordance with claim 10 wherein said aryl phosphine is a trihydrocarbyl phosphine with the proviso that at least one of the hydrocarbyl groups is phenyl or alkyl-substituted phenyl.

12. A process in accordance with claim 11 wherein said trihydrocarbyl phosphine has the structural formula $P(R^2)_x(R^3)_{3-x}$, where $R^2$ is phenyl or methylphenyl; $R^3$ is alkyl, aralkyl or alkenyl; and x is an integer of 1 to 3.

13. A process in accordance with claim 12 wherein $R^2$ is phenyl; and $R^3$ is methyl, ethyl, ethenyl or benzyl.

14. A process in accordance with claim 13 wherein $R^2$ is methylphenyl; and x is 3.

15. A process in accordance with claim 1 wherein said aryl phosphine has the structural formula $(R^4)_2P(R^5)_sP(R^4)_2$, where $R^4$ is aryl; $R^5$ is alkylene or substituted alkylene; and s is an integer of 1 to 6.

16. A process in accordance with claim 15 wherein $R^4$ is phenyl; and $R^5$ is methylene or methylene including at substituted with at least one methyl group.

17. A process in accordance with claim 16 wherein $R^5$ is —CH(CH$_3$)CH$_2$CH(CH$_3$); and s is 1.

18. A process in accordance with claim 16 wherein said aryl phosphine is bis(di-phenylphosphino)methane.

19. A process in accordance with claim 16 wherein said aryl phosphine is bis(di-phenylphosphino)britane.

20. A process in accordance with claim 1 wherein said aryl phosphine is 1,1,1-tris(diphenylphosphinomethyl) alkane.

21. A process in accordance with claim 20 wherein said aryl phosphine is 1,1,1-tris(diphenylphosphinomethyl) $C_1$ to $C_4$ alkane.

22. A process in accordance with claim 21 wherein said aryl phosphine is 1,1,1-tris(diphenylphosphinomethyl) ethane.

23. A process in accordance with claim 1 wherein said aryl phosphine is hydrogenated by contacting said aryl phosphine with hydrogen gas at a pressure above at least about 100 psi and a temperature above about 50° C.

24. A process in accordance with claim 23 wherein said aryl phosphine contacts said hydrogen gas at a temperature in the range of between about 80° C. and about 100° C. and at a pressure in the range of between about 500 psi and about 1,500 psi and wherein said aryl phosphine is dissolved in an organic solvent.

25. A process in accordance with claim 24 wherein said organic solvent is a liquid hydrocarbon and said pressure is in the range of between about 1,000 psi and about 1,400 psi.

26. A process in accordance with claim 25 wherein said liquid hydrocarbon is a $C_5$ to $C_8$ alkane and said pressure is in the range of between about 1,100 psi and about 1,300 psi.

27. A process in accordance with claim 26 wherein $C_5$ to $C_8$ alkane is cyclohexane.

28. A process for making a cyclohexylphosphine comprising hydrogenating an aryl phosphine in the presence of an effective amount of a compound having the structural formula $M(OR)_n(R^1)_{5-n}$, where M is niobium or tantalum; R is aryl or alkaryl; $R^1$ is alkyl, aralkyl, alkarylalkyl, silylalkyl, hydrogen or halogen; and n is 2 or 3.

29. A process in accordance with claim 28 wherein said aryl phosphine is selected from the group consisting of a compound having the structural formula $P(R^2)_x(R^3)_{3-x}$, where $R^2$ is aryl or alkaryl; $R^3$ is alkyl, aralkyl or alkenyl; and x is an integer of 1 to 3, a compound having the structural formula $(R^4)_2P(R^5)_sP(R^4)_2$, where $R^4$ is aryl; $R^5$ is alkylene or substituted alkylene; s is an integer of 1 to 6, and tris(diphenylphosphinomethyl)alkane.

30. A process in accordance with claim 29 wherein $R^3$ is phenyl or methylphenyl; $R^3$ is methyl, ethyl, benzyl or ethenyl; $R^4$ is phenyl; $R^5$ is methylene and said tris(diphenylphosphinomethyl)alkane is tris(di-phenylphosphinomethyl)ethane.

31. A process in accordance with claim 30 wherein said aryl phosphine is hydrogenated by contacting said hydrogen gas in an organic solvent at a pressure above about 100 psi and a temperature above about 50° C.

32. A process in accordance with claim 31 wherein R is di-$C_1$ to $C_4$ alkylphenyl di-$C_3$ to $C_8$ cycloalkylphenyl or diphenylphenyl; and $R^1$ is $C_1$ to $C_4$ alkyl, benzyl, phenylbenzyl, $C_1$–$C_2$ alkylberrzyl, $C_1$–$C_2$ alkylsilylmethyl, hydrogen or chlorine.

33. A process in accordance with claim 32 wherein said aryl phosphine is dissolved in a liquid hydrocarbon and contacts said hydrogen gas at a pressure in the range of between, about 500 psi and about 1,500 psi and a temperature in the range of between about 80° C. and about 100° C.

34. A process in accordance with claim 33 wherein R is 2,6-di-$C_1$ to $C_3$ alkylphenyl, 2,6-di-$C_3$ to $C_6$ cycloalkylphenyl or 2,6-diphenylphenyl; and $R^1$ is methyl, benzyl, trimethylsilylmethyl, 4-methylbenzyl, 4-phenylbenzyl, hydrogen or chlorine.

35. A process in accordance with claim 34 wherein said aryl phosphine is dissolved in a $C_5$ to $C_8$ alkane and contacts said hydrogen gas at a pressure in the range of between about 1,000 psi and about 1,400 psi.

36. A process in accordance with claim 35 wherein M is niobium and n is 2.

37. A process in accordance with claim 36 wherein said aryl phosphine is dissolved in cyclohexane and contacts said hydrogen gas at a pressure in the range of between about 1,100 psi and about 1,300 psi.

38. A process in accordance with claim 37 wherein $R^1$ is chlorine and said hydrogenation of said aryl phosphine takes place in a catalytically effective amount of a compound selected from the group consisting of $LiR^6$, $MgR^6_2$, $MgClR^6$, $ZnR_{63}$, sodium boron hydride, lithium boron hydride, lithium aluminum hydride, lithium aluminum triethyl hydride and diisobrityl aluminum hydride.

* * * * *

UNITED STATES PATENT AND TRADEMARK OFFICE
CERTIFICATE OF CORRECTION

PATENT NO. : 5,530,162
DATED : June 25, 1996
INVENTOR(S) : Ian P. Rothwell, et al.

It is certified that error appears in the above-indentified patent and that said Letters Patent is hereby corrected as shown below:

Column 2, line 59: "($ORT^7$)" should read --($OR^7$)--

Column 3, line 4: "$R^{13}R^{14}$" should read --$R^{13}_2R^{14}$--

Column 8, line 28: "$^3P$" should read --$^{31}P$--

Column 8, line 60: "aryl!" should read --aryl--

Column 9, line 2: "$^3p$" should read --$^{31}p$--

Column 9, line 5: "(trains)" should read --(trans)--

Column 11, line 1, Claim 30: "$R^3$" should read --$R^2$--

Column 12, line 18, Claim 38: "$ZnR_{63}$," should read --$ZnR^6_3$,"--

Signed and Sealed this

Twenty-ninth Day of April, 1997

BRUCE LEHMAN

Attest:

Attesting Officer

Commissioner of Patents and Trademarks